United States Patent [19]

Kim

[11] Patent Number: 4,655,223

[45] Date of Patent: Apr. 7, 1987

[54] FRENOTOMY METHOD AND APPARATUS

[76] Inventor: Daniel S. Y. Kim, 16103 NE. 33rd Ave., Ridgefield, Wash. 98642

[21] Appl. No.: 762,766

[22] Filed: Aug. 5, 1985

[51] Int. Cl.$^4$ .................. A61B 17/04; A61B 17/28
[52] U.S. Cl. .............................. 128/334 R; 128/321; 128/305; D24/27
[58] Field of Search ................. 128/334 R, 321, 309, 128/327, 305, 335; D24/26, 27

[56] References Cited

U.S. PATENT DOCUMENTS

| 669,034 | 2/1901 | Manly | 128/334 R |
| 755,921 | 3/1904 | O'Neill | 128/334 R |
| 4,088,134 | 5/1978 | Mazzariello | 128/321 |

FOREIGN PATENT DOCUMENTS 0424807 2/1926 Fed. Rep. of Germany ... 128/334 R

Primary Examiner—Richard C. Pinkham
Assistant Examiner—Gary Jackson
Attorney, Agent, or Firm—Chernoff, Vilhauer, McClung & Stenzel

[57] ABSTRACT

A frenotomy is performed by first injecting an infiltrating anesthesia between the superficial tissue of the frenum and the underlying muscles, the anesthesia thereby undermining the frenum and separating the superficial tissue from the underlying muscles. The undermined frenum tissue is then crimped with an instrument having crimping jaws pierced by adjacent longitudinal scalpel guide slots and two rows of adjacent suture guide holes bounding the slots. As the frenum is crimped, the slots are aligned such that a scalpel passing through, and along, the length of the slots, will sever the crimped frenum at the desired location. Prior to severing the frenum, opposing sides of the crimped frenum bounding the incision site are sutured by passing a suturing needle through the suture guide holes. The frenum is then severed between the resulting rows of sutures by passing a scalpel through, and along the length of, the adjacent scalpel guide slots. The instrument is then removed.

15 Claims, 9 Drawing Figures

U.S. Patent   Apr. 7, 1987   Sheet 1 of 2   4,655,223
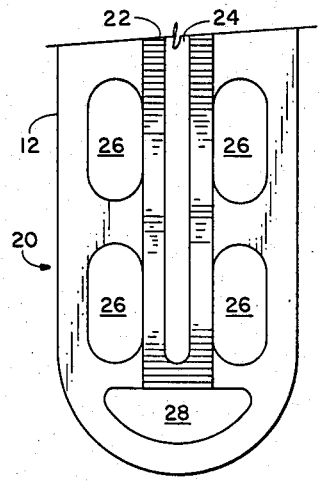
FIG. 2
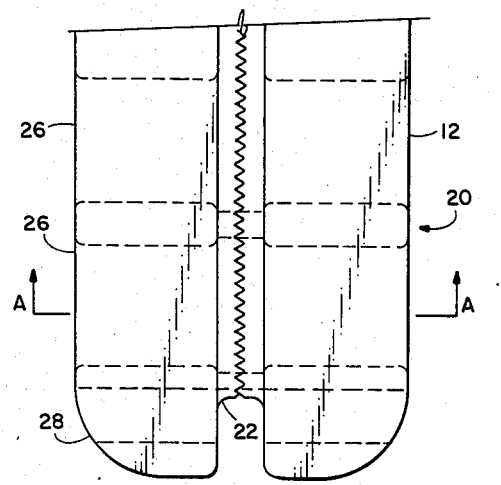
FIG. 3
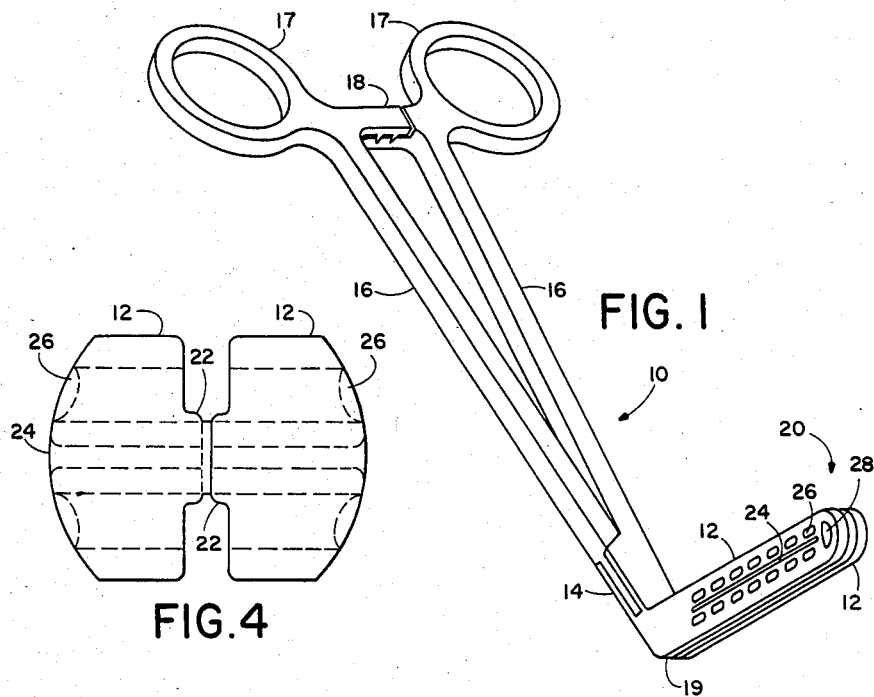
FIG. 4
FIG. 1

FRENOTOMY METHOD AND APPARATUS

BACKGROUND OF THE INVENTION

The present invention relates to surgical devices in general and in particular to a method and apparatus for performing a frenotomy.

The lingual frenum is a short fibrous length of mucosa which connects the posterior portion of the under side of the tongue to the genioglossus muscle in the floor of the mouth. Ankyloglossia (tonguetie) is a condition wherein the lingual frenum extends too far toward the tip of the tongue, attaching the tip of the tongue to the floor of the mouth, making normal speech impossible by limiting the motion of the tongue. Ankyloglossia may be treated by a lingual frenotomy (also known as an ankylotomy) wherein the anterior portion of the over extended lingual frenum is severed to free the tip of the tongue.

A frenotomy is typically performed by first pulling upward on the tongue to make taut the short fibrous lingual frenum and the underlying genioglossus muscle. The frenum, and any portion of the genioglossus muscle extending into the frenum, are then severed with scissors midway between the tip of the tongue and the origin of the frenum, the lingual surface of the symphysis of the mandible. The cut is directed posteriorly parallel to the floor of the oral cavity, extending inward for a sufficient distance (typically 1.5 to 3 cm) to allow the tip of the tongue to touch the lingual surfaces of the maxillary anterior teeth with the mouth open. The lateral edges of the surgical incision are then undermined with the scissors to separate the mucosa from the underlying muscles. The cut edges of mucosa in the floor of the mouth and on the under surface the tongue are then sutured such that the horizontal incision becomes a vertical one.

The method of the prior art is effective but has some drawbacks. It is difficult to obtain a well directed incision and the incision and undermining cause profuse bleeding, along with rolled, irregular and mismatched incision edges, making accurate suturing difficult. Also the undermining and subsequent handling of the mucosa cause a large amount of tissue damage, resulting in more postoperative swelling and pain.

SUMMARY OF THE INVENTION

According to one aspect of the invention, a lingual frenotomy is performed by first injecting an infiltrating anesthesia between the superficial tissue of the lingual frenum and the underlying muscles, the anesthesia thereby undermining the frenum, separating the superficial tissue from the underlying muscles.

According to another aspect of the invention, the undermined superficial frenum tissues are then crimped with an instrument comprising a pair of crimping jaws pierced by two rows of adjacent suture guide holes bounding slots. As the frenum is crimped, the guide hole rows are aligned such that they bound the site of an incision to be made in the frenum. With the crimping jaws in place on the frenum, opposing sides of the crimped frenum are sutured by passing a suturing needle through guide holes.

According to still another aspect of the invention, the jaws of the frenum crimping apparatus are also pierced by adjacent scalpel guide slots bounded by the two rows of adjacent suture guide holes. After the frenum is sutured, it is severed between the suture rows by passing a scalpel through, and along the length of, the adjacent scalpel guide slots. The frenum crimping apparatus is then removed.

The method and apparatus of the present invention permit accurate severing and suturing of the frenum because the scalpel guide slots and suture guide holes can be easily and accurately positioned on the frenum. Because the frenum is sutured before the incision is made, and because the jamming of the frenum tissue by the crimping jaws during suturing closes blood vessels and facilitates blood coagulation at the cut endings, there is little (almost no) bleeding following the incision. The injection method of undermining and the resulting reduction in handling of the tissues minimizes tissue damage so that postoperative pain and swelling are limited. Because the use of the frenum crimping apparatus simplifies the incision and suturing process, the method and apparatus of the present invention permit frenotomies to be performed more rapidly and by those with less surgical skill than is permitted by methods and apparatus of the prior art.

It is accordingly an object of the present invention to provide a new and improved method and apparatus for performing a frenotomy, allowing accurate incision of the frenum.

It is another object of the present invention to provide a new and improved method and apparatus for performing a frenotomy allowing accurate suturing of the frenum.

It is still another object of the present invention to provide a new and improved method and apparatus for performing a frenotomy wherein the amount of bleeding is minimized.

It is a further object of the present invention to provide a new and improved method and apparatus for performing a frenotomy wherein post-operative pain and swelling are minimized.

It is a still further object of the present invention to provide a new and improved method and apparatus for performing a frenotomy wherein the required level of surgical skill is reduced.

It is yet another object of the present invention to provide a new and improved method and apparatus for performing a frenotomy rapidly.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DRAWINGS

FIG. 1 is a perspective view of the frenum crimping apparatus of the present invention, FIG. 2 is a side view of the tip portion of the frenum crimping apparatus of FIG. 1, FIG. 3 is a forward view of the tip portion of the frenum crimping apparatus of FIG. 1, FIG. 4 is an end view of the tip portion of the frenum crimping apparatus of FIG. 1, FIG. 5 is a drawing of a severe ankyloglossia in a patient prior to a lingual frenotomy, FIG. 6 shows the frenum crimping apparatus of FIG. 1 in place on a lingual frenum of FIG. 5 during a frenotomy in accordance with the present invention, FIG. 7 shows the cutting of the frenum of FIG. 6 according to the present invention, FIG. 8 shows the underside of the tongue of the patient of FIG. 5 following a lingual frenotomy according to the present invention, and FIG. 9 illustrates suturing of the frenum.

DETAILED DESCRIPTION

Figure 5:
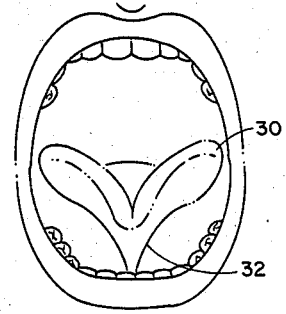

Referring to FIG. 1, a frenum crimping apparatus 10, illustrated in perspective view, is adapted for use during a lingal frenotomy performed in accordance with the method of the present invention. Frenum crimping apparatus 10 comprises a pair of jaws 12 for gripping the frenum and handles 16, with finger rings 17, for opening and closing jaws 12. The handles are hinged at 14 and extend at an angle of approximately 135 degrees to jaws 12, being joined to jaws 12 at 19. Interlocking tabs 18 on handles 16 hold jaws 12 closed until released by flexing handles 16 to separate tabs 18. Each jaw 12 is approximately 3 cm long and approximately 5.5 mm wide, while handles 16 are approximately 8 cm long down to hinge 14. When jaws 12 grip the frenum, handles 16 extend downwards to avoid obstructing access to the mouth.

FIG. 2 is a view of the inner side of the tip portion 20 of one jaw 12 while FIG. 3 is a forward view of tip portions 20 of both jaws 12. FIG. 4 is an end view of tip portion 20 of both jaws with dashed lines indicating a cross-section at A—A in FIG. 3. Referring to FIGS. 2-4, a raised gripping strip 22, approximately 0.9 mm wide, extends along the center line of the inner surface of jaw 12, terminating approximately 3 mm from the end of the jaw tip. The surface of gripping strip 22 is cross-hatched or serrated to improve the tissue griping characteristics of the strip. A scalpel guide slot 24, approximately 0.3 mm wide, passes through each jaw 12, coextensive with the center lines of gripping strips 22. On either side of each gripping strip 22 are rows of adjacent suture guide holes 26, each approximately 1.5 mm wide and 3 mm long. Another suture guide hole 28 is located at the end of each frenum crimping apparatus tip portion 20. The guide holes and slots are suitably flared at the outer surfaces of jaws 12.

FIG. 5 is a view of the tongue of a patient exhibiting severe ankyloglossia, a condition wherein the central portion of the under side of tongue 30 is attached to the floor of the mouth by an unusually wide fibrous lingual frenum 32 extending from the tip to the root of tongue 30. With the mouth open and the tongue held up, a lingual frenotomy according to method of the present invention is performed by first injecting an infiltrating anesthesia between the superficial tissue of lingual frenum 32 and the underlying muscles, the anesthesia thereby undermining the frenum, separating the superficial tissues from the underlying muscles.

The superficial tissues of frenum 32 are then crimped with the frenum crimping apparatus 10, the scalpel guide slots 24 of frenum crimping apparatus 10 being aligned such that a scalpel passing through, and along, the length of the slots, will sever frenum 32 midway between the tip of tongue 30 and it origin, the lingual surface of the symphysis of the mandible, the cut being directed posteriorly parallel to the floor of the oral cavity for a distance of 1.5 to 3 cm as sufficient to allow the tip of the tongue to touch the lingual surfaces of the maxillary anterior teeth with the mouth open.

Figure 6:
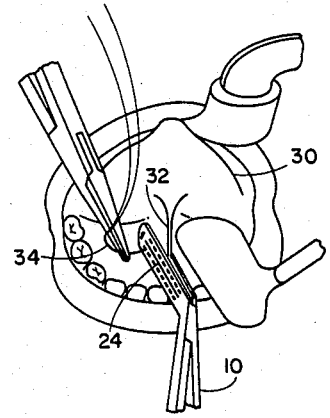
Figure 7:
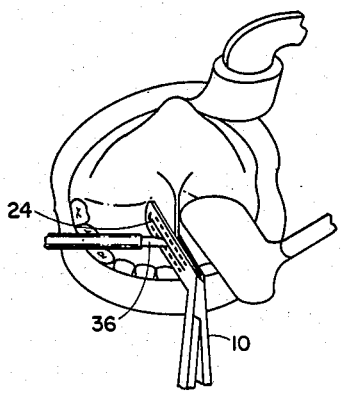
Figure 8:
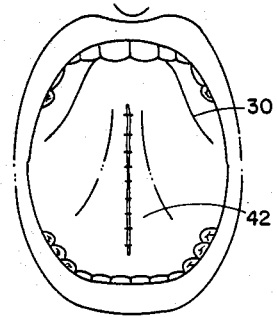
Figure 9:
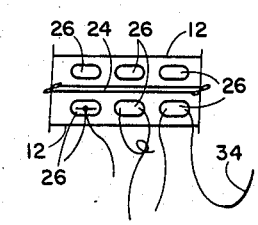

With the frenum crimping apparatus 10 in place on the frenum 32, as depicted in FIGS. 6 and 7, and prior to severing the frenum, opposing sides of the frenum are sutured, in the locations defined by suture guide holes 26 and 28 (of FIGS. 2-4), by passing a suturing needle 34 (FIG. 6) through the suture guide holes. A non-continuous or interrupted suture is suitably completed for each hole or pair of facing holes as illustrated in FIG. 9. The adjacent sutures in the drawing illustrate three stages in suturing, proceeding from right to left. Frenum 32 is then severed as shown in FIG. 7, by passing scalpel blade 36 through, and along the length of, slots 24 of frenum crimping apparatus 10. Frenum crimping apparatus 10 is then removed from frenum 32. FIG. 8 shows the resulting incision and sutures 42 on the under side of tongue 30 and in the floor of the mouth.

In the preferred embodiment, frenum crimping apparatus 10 is intended for use in a lingual frenotomy. However, this type of apparatus may be used in performing a frenectomy of the upper labial frenum, following substantially the same procedure. While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

I claim:

1. A method for performing a frenotomy comprising the following steps:
    a. suturing the frenum with two adjacent rows of sutures, and
    b. severing the frenum between the suture rows, step a occurring before step b.

2. A method as in claim 1 further comprising the step of:
    c. undermining the frenum prior to suturing by injecting a fluid beneath the superficial tissues of the frenum, step c occurring before step a.

3. The method of claim 1, wherein said sutures in said rows are substantially elongate and substantially coaxial with the respective one of said rows.

4. A method for performing a frenotomy comprising the following steps:
    (a) clamping the frenum with a pair of jaws, each having a suture guide hole, said holes being aligned, and
    (b) suturing the clamped frenum by passing a suturing needle through said aligned guide holes.

5. The method of claim 4 including forming a suture loop in the clamped frenum within said aligned guide holes.

6. A method for performing a frenotomy comprising the following steps:
    (a) clamping the frenum with a pair of jaws, each having a longitudinal slot said slots being aligned, and
    (b) severing the clamping frenum by passing a blade through said aligned slots.

7. A method for performing a frenotomy comprising the following steps:
    a. clamping the frenum with a pair of jaws having adjacent suture guide holes and adjacent scalpel guide slots,
    b. suturing the clamped frenum by passing a suturing needle through the guide holes, and
    c. severing the clamped frenum by passing a blade through the adjacent guide slots.

8. A method for performing a frenotomy as in claim 7 further comprising the step of:
   d. undermining the frenum by injecting a fluid beneath the superficial tissues of the frenum prior to step a.

9. A method for performing a frenotomy as in claim 7 wherein two rows of adjacent holes pass through the jaws, the hole rows bounding the slots.

10. A method for performing a frenotomy comprising the following steps:
   a. undermining the frenum by injecting a fluid beneath the superficial tissues of the frenum,
   b. clamping the frenum with a pair of jaws having adjacent longitudinal slots and two rows of adjacent holes passing through the jaws, the hole rows bounding the slots,
   c. suturing the superficial tissues of the frenum by passing a suturing needle through the holes, and
   d. severing the superficial tissues of the frenum by passing a blade through the adjacent slots.

11. An apparatus for facilitating a frenotomy comprising:
   (a) a pair of opposed jaws;
   (b) each of said jaws including a first elongate row of suture guide holes; and
   (c) each of said jaws also including an elongate slot substantially parallel to said first row of said suture guide holes.

12. The apparatus of claim 11, wherein each of said jaws includes a second elongate row of suture guide holes substantially parallel to said first row, said slot interposed between said first and second rows.

13. The apparatus of claim 12, wherein each of said jaws includes a suture guide hole proximate one end of said slot so that said suture guide holes define a U-shaped suture line substantially enclosing said end of said slot.

14. The apparatus of claim 11 wherein said first row and said slot of one of said jaws are aligned with said first row and said slot of said other one of said jaws.

15. The apparatur os claim 11, wherein each of said jaws include a clamping surface interposed between said first row and said slot.

* * * * *

UNITED STATES PATENT AND TRADEMARK OFFICE
CERTIFICATE OF CORRECTION

PATENT NO. : 4,655,223

DATED : April 7, 1987

INVENTOR(S) : Daniel S. Y. Kim

It is certified that error appears in the above-identified patent and that said Letters Patent is hereby corrected as shown below:

Col. 6, line 19    Change "apparatur" to --apparatus--

Col. 6, line 19    Change "os" to --of--

Signed and Sealed this

Third Day of November, 1987

Attest:

DONALD J. QUIGG

Attesting Officer    Commissioner of Patents and Trademarks